United States Patent [19]
Shriver et al.

[11] 3,966,955
[45] June 29, 1976

[54] ANTI-ULCER THERAPY

[75] Inventors: David A. Shriver, King of Prussia; Melvyn I. Gluckman, Wayne, both of Pa.

[73] Assignee: American Home Products Corporation, New York, N.Y.

[22] Filed: Aug. 7, 1974

[21] Appl. No.: 495,353

[52] U.S. Cl. .............................................. 424/273
[51] Int. Cl.² ...................................... A61K 31/415
[58] Field of Search .................................... 424/273

[56] References Cited
UNITED STATES PATENTS

| | | | |
|---|---|---|---|
| 3,759,994 | 9/1973 | Diamond et al. | 424/326 X |
| 3,763,178 | 10/1973 | Sulkowski | 424/273 X |
| 3,803,155 | 4/1974 | Sulkowski et al. | 424/273 X |

OTHER PUBLICATIONS

Experientia 24/11, pp. 1151–1155, (1968).

*Primary Examiner*—Frederick E. Waddell
*Attorney, Agent, or Firm*—Stephen Venetianer

[57] ABSTRACT

A method of treating gastric ulcers in a warm-blooded animal with salts of an imidazolinyl phenyl carbonyl compound or a dihydroimidazoisoindolol is disclosed.

1 Claim, No Drawings

ANTI-ULCER THERAPY

SUMMARY OF THE INVENTION

This invention relates generally to a method of treating ulcers in warm-blooded animals. More particularly, the invention relates to a method which utilizes the administration to warm-blooded animals of a compound selected from a group of compounds defined below, which compounds have been found to have unexpected anti-ulcer activity.

DESCRIPTION OF THE INVENTION

We have now discovered that a particular group of compounds, previously known to be useful primarily as anorexiants and antidepressants, suprisingly are highly effective anti-ulcer agents. The invention, in its broadest concept, resides in the method of treating an ulceration in a warm-blooded animal by administering to the animal a therapeutically active amount of a compound selected from the group consisting of those having the following general formulae:

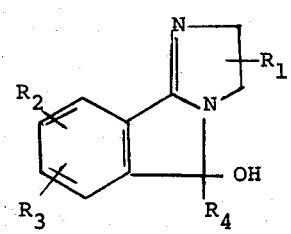

(I)

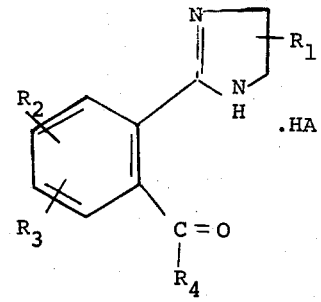

(II)

wherein $R_1$ is hydrogen or lower alkyl;

$R_2$ is selected from the group consisting of hydrogen, halogen, amino, lower alkylamino, lower alkyl, and lower alkoxy; $R_3$ is hydrogen when $R_2$ and $R_3$ are dissimilar and when $R_2$ and $R_3$ are the same they are both selected from the group consisting of hydrogen, halogen, lower alkyl, and lower alkoxy; R is selected from the group consisting of phenyl, monohalophenyl, dihalophenyl, mono(lower)alkylphenyl, di(lower)alkyl-phenyl, trifluoro-methylphenyl, mono(lower)alkoxyphenyl, and di(lower) alkoxyphenyl; and HA is a pharmaceutically acceptable acid. Such compounds where $R_1$ is hydrogen are disclosed and claimed in U.S. Pat. No. 3,763,178, issued Oct. 2, 1973, incorporated herein by reference. Such compounds where $R_1$ is lower alkyl are disclosed in Belgian Pat. No. 712,958, published Sept. 10, 1969, incorporated herein by reference.

As employed herein the term (lower)alkyl includes straight and branched chain hydrocarbon moieties of from 1 to about 4 carbon atoms such as methyl, ethyl, propyl, i-propyl and butyl. The term (lower)alkoxy includes hydrocarbonoxy groups which contain from 1 to about 6 carbon atoms such as methoxy ethoxy, propoxy, butoxy and hexoxy. The term "halogen" and "halo" as used herein include bormine, fluorine, chlorine and iodine.

The dihydroimidazoisoindolols used in the process of this invention may be synthesized by the following schematic sequence of reactions:

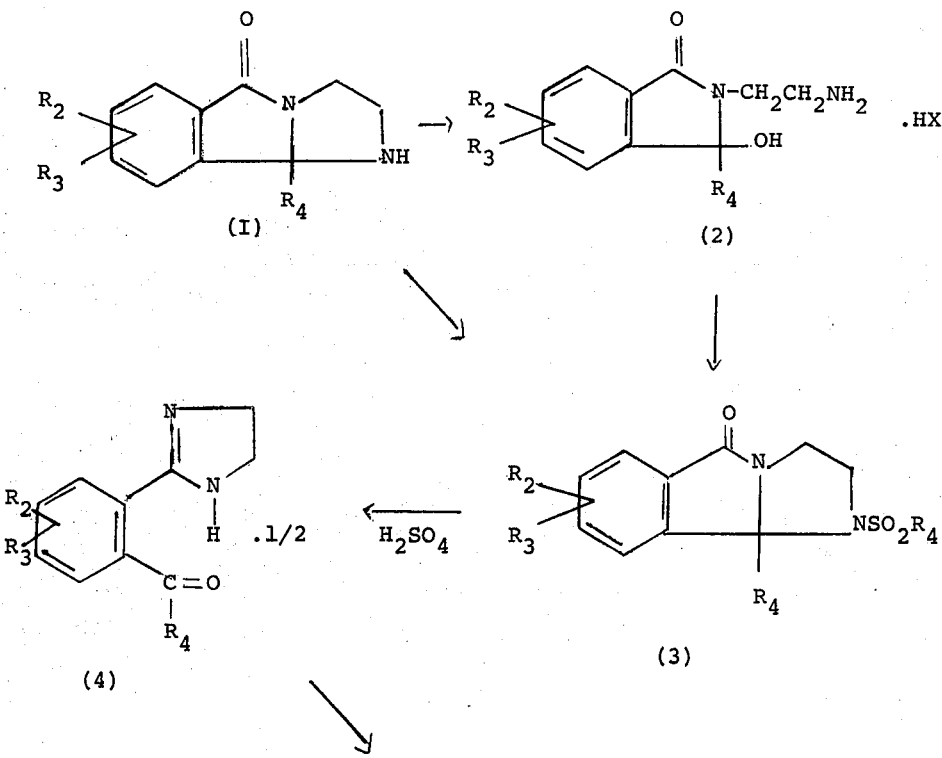

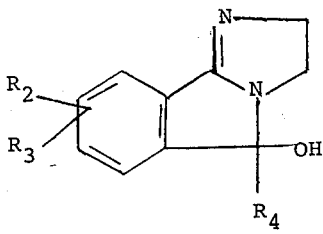

(5)

wherein $R_2$, $R_3$ and $R_4$ are defined as above, $R_6$ is aryl and alkyl, for example: lower alkyl, phenyl, monohalophenyl, dihalophenyl, mono(lower)alkylphenyl, di(lower)alkylphenyl and alkoxyphenyl, and X is the anion portion of a mineral acid. The rearrangement of a tetrahydroimidazoisoindolone of Formula 1 is effected by contacting the particular Compound 1 with a mineral acid. This reaction may be accelerated by heating and stirring the reaction mixture until the precipitation of the 2-(aminoethyl)-3-hydroxyphthalimidine mineral acid addition salt, as designated in Formula 2, is complete. The phthalimidine (2) is separated by filtration or decantation and either recrystallized from a suitable solvent, such as water, a lower alkanol and dioxan, or admixed directly with a substantially equimolar quantity of an aryl or alkyl sulfonyl halide in pyridine. The reaction mixture is then heated to a temperature from about 80°C. to about 115°C. for a period from about two hours to about ten hours. Preferably, this reaction is conducted at the reflux temperature of the reaction mixture for a period of about two hours. After the above reaction is complete, the product of sulfonyltetrahydroimidazoisoindolone (3) is recovered by customary isolation procedures.

The above prepared sulfonyltetrahydroimidazoisoindolone (3) may be hydrolyzed and rearranged by admixture with from about 80 to about 100 percent sulfuric acid. The product of this hydrolysis, the sulfate salt of an imidazolinyl phenyl carbonyl compound, is shown in Formula 4 which may be recovered as such by conventional means. Alternatively, the reaction mixture is neutralized by the addition of a base and the resulting precipitate recrystallized from an appropriate organic solvent such as lower alkanol, dioxan, dimethylformamide and dimethylacetamide to afford an appropriate dihydroimidazoisoindolol (5).

An alternative process for the preparation of the compounds useful in the process of this invention is described and claimed in U.S. Pat. No. 3,803,155, issued Apr. 9, 1974, incorporated herein by reference.

For preparing compounds useful in this invention where $R_1$ is lower alkyl, the above procedure can be employed except that there is used instead a substituted phthalimidine of the formula:

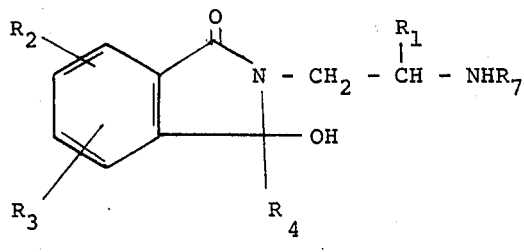

wherein $R_1$, $R_2$, $R_3$, and $R_4$ are defined as above and $R_7$ is lower alkylsulfonyl, phenylsulfonyl, monohalophenylsulfonyl, dihalophenylsulfonyl, mono(lower)alkylphenylsulfonyl, di(lower)alkoxyphenylsulfonyl.

The substituted phthalimidines can be prepared by the sulfonylation of the intermediate phthalimidine compound. The intermediate phthalimidines are readily prepared by reacting a Ω acid chloride of an o-aroyl benzoic acid with the appropriate substituted or unsubstituted ethylene diamine compound. These type compounds are described in the literature. (Sulkowski et al J. Org. CHem. 32, 2180).

They are cyclized to a 2-(2-imidazolin-2-yl)benzophenone by treatment with sulfuric acid according to the procedure outlined above.

For example, the compound referred to hereinafter as Compound 7 is prepared as follows:

A solution of 25 g of a o-(p-fluorobenzoyl)benzoic acid, 75 ml. of toluene, and 40 ml of 1,2-diaminopropane is refluxed in a flask equipped with a water separator. After refluxing 19 hours, the solution is extracted with water then evaporated to dryness. The residue solidifies on standing, mp. 115°–120°C. The residue consists of 9b-(p-fluorophenyl)-2-methyl)-1,2,3,9b-tetrahydro-5H[2,1-a]isoindol-5-one as the major product together with some 3-methyl isomer.

A solution of 38 g of the mixture from above, 32 g of p-toluenesulfonyl chloride and 125 ml of pyridine is refluxed for 19 hours. The mixture is evaporated to dryness and the residue is dissolved in 100 ml of ethanol. After standing 18 hours, the precipitated solid is separated and recrystallized twice from ethanol to obtain 9b-(p-fluorophenyl)-2-methyl-1,2,3,9b-tetrahydro-1-(p-tolylsulfonyl)-5H-imidazo[2,1-a]isoindol-5-one, mp. 215°–7°C.

Anal. Calcd for $C_{24}H_{21}N_2FSO_3$: C, 66.04; H, 4.85; N, 6.42. Found: C, 66.17; H, 4.79; N, 6.17.

A solution of 25 g of 9b-(p-fluorophenyl)-2-methyl-1,2,3,9b-tetrahydro-1-(p-tolylsulfonyl)-5H)-imidazo[2,1-a]isoindol-5-one and 100 ml of 90% sulfuric acid is allowed to stand at room temperature for 45 minutes. The mixture is quenched with several volumes of ice water and neutralized with con. sodium hydroxide solution. The solid is separated and washed with water. On recrystallization from ethanol there is obtained 5-(p-fluorophenyl)-2,3-dihydro-2(3)methyl-5H-imidazo[2,1-a]isoindol-5-ol, mp. 168°–170°C.

Anal. Calcd for $C_{17}H_{15}FN_2O$: C, 72.32; H, 5.35; N, 9.92. Found: C, 72.25; H, 5.36; N, 9.66.

TEST PROCEDURE

The compounds were tested according to a modification of the method described by D. A. Brodie and H. Hanson in Journal of Applied Physiology, Vol. 15, pages 291–294 (1960).

Male Charles River rats weighing between 120–160 gm. are deprived of food for 18 hr. with water ad lib. The rats are divided into groups of ten and dosed by the oral route with test compound, 50 ml/kg, or vehicle control, 0.5% carboxymethylcellulose; in a volume of 5 ml/kg. Immeditely after dosing the animals are inserted into aluminum restraining tubes measuring 1 5/8 inche-sin diameter by 8 inches and placed in the cold (4° ± 1°C.). The time in the cold is adjusted so that 90 percent of the control animals exhibit ulcers. At the end of the test period the animals are killed, the duodenum and esophagus ligated, and the stomach removed. The stomachs are inflated with water, opened along the lesser curvature spread over the index finger, and the mucosa wiped off to expose the submucosa. The number of hemorrhage sites in the submucosa are counted by visual observation and recorded; however, since these numbers are so variable, only the incidence of ulcer (i.e., the number of rats with ulcers) are used for evaluation.

Compounds are reported by determining a percent inhibition which is calculated as follows:

$$\frac{\% \text{ rats with ulcers in control} - \% \text{ rats with ulcers in treatment}}{\% \text{ rats with ulcers in control}} \times 100 = \% \text{ inhibition}$$

Compounds with a greater than 70 percent inhibition are significantly different from the control group using a corrected Chi square analysis.

COMPOUNDS TESTED 1. 5-(p-chlorophenyl)-2,5-dihydro-3H-imadazo[2,1-a]isoindol-5-ol ($R_1$, $R_2$, $R_3$ = H; $R_4$ = p-chlorophenyl)
2. 2,5-dihydro-5-phenyl-3H-imidazo[2,1-a]isoindol-5-ol ($R_1$, $R_2$, $R_3$ = H; $R_4$ = phenyl).
3. 5-(3,4-dichlorophenyl)-2,5-dihydro-3H-imidazo[2,1-a]-isoindol-5-ol ($R_1$, $R_2$, $R_3$ = H; $R_4$ = 3,4-dichlorophenyl).
4. 5-(3-bromo-p-tolyl)-2,5-dihydro-3H-imidazo[2,1-a]-isoindol-5-ol ($R_1$, $R_2$, $R_3$ = H; $R_4$ = 3-bromo-p-tolyl).
5. 5-(p-fluorophenyl)-2,3-dihydro-5H-imidazo[2,1-a]isonindol-5-ol ($R_1$, $R_2$, $R_3$ = H; $R_4$ = p-fluorophenyl).
6. 2,3-dihydro-5-(p-tolyl)-5H-imidazo[2,1-a]isondol-5-ol ($R_1$, $R_2$, $R_3$ = H; $R_4$ = p-tolyl).
7. 5-(p-fluorophenyl)-2,3-dihydro-2 (or 3)-methyl-5H-imidazo [2,1]isonindol-5-ol ($R_1$ = methyl; $R_2$, $R_3$ = H; $R_4$ = p-fluorophenyl).
8. 2-[4(or 5)-methyl 1-2-imidazolin-2-yl]-3-trifluoromethylbenzophenone, hydrochloride ($R_1$ = methyl; $R_2$, $R_3$ = H; $R_4$ = 3-trifluoromethylphenyl).
9. 2,3-dihydro-5-(p-hydroxyphenyl)-5H-imidazo[2,1-a]isoindol-5-ol ($R_1$, $R_2$, $R_3$ = H; $R_4$ = p-hydroxyphenyl).
10. 5-(3,5-dichlorophenyl)-2,3-dihydro-5H-imidazo[2,1-a]-isoindol-5-ol ($R_1$, $R_2$, $R_3$ = H; $R_4$ = 3,5-dichlorophenyl).
11. 3'-chloro-2-(4[or 5]-methyl-2-imidazolin,2-yl)benzophenone, hydrochloride ($R_1$ = methyl; $R_2$, $R_3$ = H; $R_4$ = 3-chlorophenyl).
12. 2'-chloro-2-(4[or 5]-methyl-2-imidazolin-2-yl)benzophenone, hydrochloride ($R_1$ = methyl; $R_2$, $R_3$ = H; $R_4$ = 2-chlorophenyl).
13. 2-(2-imidazolin-2-yl)-4'-trifluoromethylbenzophenone, hydrochloride ($R_1$, $R_2$, $R_3$ = H; $R_4$ = 4-trifluoromethylphenyl).
14. 2-(2-imidazolin-2-yl)-3'-trifluoromethylbenzophenone, hydrochloride ($R_1$, $R_2$, $R_3$ = H; $R_4$ = 3-trifluoromethylphenyl).

| Compound | TEST RESULTS Dose (mg/kg) | % Inhibition |
|---|---|---|
| 1 | 0.10 | 10 |
|  | 0.25 | 40 |
|  | 0.50 | 70 |
|  | 1.0 | 90 |
|  | 10.0 | 100 |
|  | 25.0 | 50 |
| 2 | 25.0 | 67 |

| Compound | -continued TEST RESULTS Dose (mg/kg) | % Inhibition |
|---|---|---|
| 3 | 0.10 | 0 |
|  | 0.25 | 10 |
|  | 0.50 | 70 |
|  | 1.0 | 60 |
|  | 10.0 | 87.5 |
|  | 25.0 | 70 |
| 4 | 6.25 | 20 |
|  | 12.50 | 60 |
|  | 25.00 | 90 |
|  | 50.00 | 100 |
| 5 | 0.10 | 10 |
|  | 0.25 | 10 |
|  | 0.50 | 70 |
|  | 1.0 | 80 |
|  | 10.0 | 90 |
|  | 25.0 | 80 |
| 6 | 1 | 0 |
|  | 5 | 50 |
|  | 10 | 60 |
|  | 25 | 100 |
| 7 | 6.25 | 40 |
|  | 12.5 | 60 |
|  | 25 | 80 |
|  | 50 | 100 |
| 8 | 12.5 | 0 |
|  | 25 | 70 |
|  | 50 | 100 |
| 9 | 50 | 10 |
| 10 | 0.5 | 30 |
|  | 1.0 | 50 |
|  | 10.0 | 90 |
|  | 50.0 | 80 |
| 11 | 10 | 60 |
| 12 | 10 | 40 |
| 13 | — | — |
|  | 3.0 | 10 |
|  | 6.25 | 90 |
|  | 12.5 | 67 |
|  | 25.0 | 50 |
|  | 50.0 | 100 |
| 14 | — | — |
|  | 3.0 | 10 |
|  | 6.25 | 80 |
|  | 12.5 | 78 |
|  | 25.0 | 30 |
|  | 50.0 | 100 |
| L-Amphetamine Sulfate | 0.125 | 0 |
|  | 0.25 | 0 |
|  | 0.50 | 0 |
|  | 1.0 | 0 |
|  | 2.0 | 20 |
|  | 4.0 | 60 |
|  | 8.0 | 100 |

In the above tests one out of 10 rats died with compound 2, one out of 10 rats died with compound 3 at 10 mg/kg, and one out of 10 rats died with 1-amphetamine sulfate at 1 mg/kg.

The compounds of this invention may be administered alone or in combination with pharmaceutically acceptable carriers, the proportion of which is determined by the solubility and chemical nature of the compound, chosen route of administration and standard pharmaceutical practice. For example, they may be administered orally in the form of tablets or capsules containing such excipients as starch, milk, sugar, certain types of clay and so forth. They may be administered sulbingually in the form of troches or lozenges in which the active ingredient is mixed with sugar and corn syrups, flavoring agents and dyes; and then dehydrated sufficiently to make it suitable for pressing into a solid form. They may be administered orally in the form of solutions which may contain coloring and flavoring agents or they may be injected parenterally, that is intramuscularly, intravenously or subcutaneously. For parenteral administration they may be used in the form of a sterile solution containing other solutes, for example, enough saline or glucose to make the solution isotonic.

The dosage of the present therapeutic agents will vary with the form of administration and the particular compound chosen. Furthermore, it will vary with the particular subject under treatment. Generally, the treatment is initiated with small dosages substantially less than the optimum dose of the compound. Thereafter, the dosage is increased by small increments until the optimum effect under the circumstances is reached. It will generally be found that when the composition is administered orally, larger quantities of the active agent will be required to produce the same effect as a smaller quantity given parenterally. In general, the compounds of this invention are most desirably administered at a concentration level that will generally afford effective results without causing any harmful or deleterious side effects and preferably at a level that is in the range of from about 0.1 to about 100 mg/day, although, as aforementioned, variations will occur. However, a dosage level that is in the range of from about 5 to about 75 mg per day is most desirably employed in order to achieve effective results. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. The method of treating gastric ulcers in a warm blooded animal suffering from ulcers which comprises orally or parenterally administering to said animal an effective amount of a compound of the following formulae:

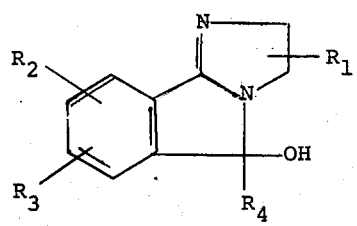 and 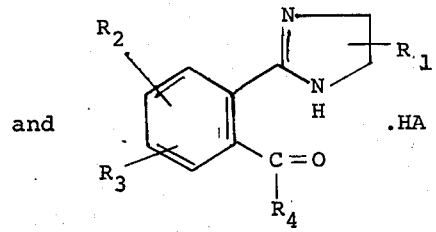

wherein
$R_1$ is hydrogen or lower alkyl;
$R_2$ is selected from the group consisting of hydrogen, halogen, amino, lower alkylamino, lower alkyl, and lower alkoxy; $R_3$ is hydrogen when $R_2$ and $R_3$ are dissimilar and when $R_2$ and $R_3$ are the same they are both selected from the group consisting of hydrogen, halogen, lower alkyl, and lower alkoxy; $R_4$ is selected from the group consisting of phenyl, monohalophenyl, dihalophenyl, mono(lower)alkylphenyl, di(lower)alkyl-phenyl, trifluoromethylphenyl, mono(lower)alkoxyphenyl, and di(lower)alkoxyphenyl; and HA is a pharmaceutically acceptable acid.

* * * * *